(12) United States Patent
Panchal

(10) Patent No.: US 8,663,707 B2
(45) Date of Patent: Mar. 4, 2014

(54) METHOD AND TREATMENT FOR THE REDUCTION OF ATHEROSCLEROSIS

(76) Inventor: Ajay J. Panchal, Los Angeles, CA (US)

(*) Notice: Subject to any disclaimer, the term of this patent is extended or adjusted under 35 U.S.C. 154(b) by 0 days.

(21) Appl. No.: 13/556,407

(22) Filed: Jul. 24, 2012

(65) Prior Publication Data

US 2014/0030363 A1  Jan. 30, 2014

(51) Int. Cl.
*A61B 17/22* (2006.01)
(52) U.S. Cl.
USPC ............ 424/709; 425/701; 514/763; 606/127
(58) Field of Classification Search
None
See application file for complete search history.

(56) References Cited

U.S. PATENT DOCUMENTS

| | | | |
|---|---|---|---|
| 6,423,742 | B1 | 7/2002 | Larson |
| 2005/0223420 | A1 | 10/2005 | Krieger et al. |
| 2006/0154252 | A1 | 7/2006 | Marguerie et al. |
| 2007/0196355 | A1 | 8/2007 | Coleman |
| 2009/0117079 | A1 | 5/2009 | Monte |
| 2011/0196383 | A1 | 8/2011 | Aziz et al. |

OTHER PUBLICATIONS

Gil-Bernabe et al., Circulation Journal; vol. 75, published online Jul. 14, 2011.*
Delmez et al., "Sodium Sulfate treatment of vascular calcification in ESRD"; published Jan. 14, 2010.*
Wald et al., BMJ.; 326. p. 7404, Published Jun. 28, 2003.*
The Police Notebook, Published Jun. 28, 2003. and Sacco et al., Title: The Protective Effect of Moderate Alcohol Consumption on Ischemic Stroke, JAMA. 1999;281(1):53-60.*
Gil-Bernabe, Paloma, et al. "Atherosclerosis Amelioration by Moderate Alcohol Consumption Is Associated With Increased Circulating Levels of Stromal Cell-Derived Factor-1", Circulation Journal, Official Journal of the Japanese Circulation Society; vol. 75, Sep. 2011, 11 pages.
Wrzolkowa, Teresa, et al. "Effects of ethanol on the development of experimental atherosclerosis and cardionescrosis in rats", Alcohol, Jul.-Aug. 1990, vol. 7, Issue 4, pp. 299-306. (Abstract) Elsevier [online]. . [retrieved on Jan. 25, 2012].
Imhof, Armin P., M.D., et al. "Alcohol, Inflammation and Atherosclerosis". [online], Oct. 1, 2008 [retrieved on Jan. 25, 2012]. Retrieved from the Internet:< URL: http://clinicaltrials.gov/ct2/show/NCT00764426>.
Rudel, L.L., et al. "Dietary ethanol-induced modifications in hyperlipoproteinemia and atherosclerosis in nonhuman primates (*Macaca nemestrina*)", Journal of the American Heart Association; Arterioscler Thromb. Vasc. Biol. 1981, 1:144-155, 1981, 13 pages. Retrieved from the Internet: < URL: http://atvb.ahajournals.org/content/1/2/144>.
Delmez, James A., M.D.. "Sodium Thiosulfate Treatment of Vascular Calcification in ESRD". [online], Jan. 14, 2010 [retrieved on Jan. 25, 2012]. Retrieved from the Internet< URL: http://clinicaltrials.gov/ct2/show/NCT00568399>.

\* cited by examiner

*Primary Examiner* — Anoop Singh
*Assistant Examiner* — Yanzhi Zhang
(74) *Attorney, Agent, or Firm* — Schmeiser, Olsen & Watts, LLP

(57) ABSTRACT

A method for treating atherosclerosis in a patient comprising maintaining an elevated level of alcohol in the patient's blood; and administering a calcium chelating agent is provided.

18 Claims, 2 Drawing Sheets

METHOD AND TREATMENT FOR THE REDUCTION OF ATHEROSCLEROSIS

FIELD OF TECHNOLOGY

The following relates to a method for the treatment and reduction of atherosclerosis. More specifically, the following relates to the use of high doses of ethanol over a prolonged period of time in combination with a calcium chelating agent. Additionally, the following relates to a method for inducing atherosclerosis in mammals.

BACKGROUND

Cardiovascular diseases are one of the primary causes of death in industrialized countries. Examples of cardiovascular diseases include coronary artery disease, peripheral artery disease, heart attack, and stroke. Atherosclerosis is one of the underlying causes of cardiovascular diseases, and essentially is the accumulation of plaque on the interior walls of arteries. Plaque deposits consist of white blood cells, calcium, cholesterol, and other connective tissues. The accumulation of plaque results in a hardening of the arterial walls, as well as a narrowing of the interior of the arteries, resulting in a decrease, or even total occlusion, of blood flow through the arteries.

There are many different theories as to the cause of atherosclerosis, including elevated levels of cholesterol, inflammation and damage to arterial walls, or genetic predisposition. Treatment of atherosclerosis generally consists of changes in diet and exercise, the use of medications such as statins to reduce cholesterol levels, or surgery, such as angioplasty or bypass surgery. Medications, such as statins, and treatment involving behavioral and dietary changes primarily seek to prevent plaque accumulation, but may not help to reduce atherosclerosis once it has developed. In addition, surgical treatments effect only physical changes, such as compressing plaque deposits to open up occluded arteries in the case of angioplasty, or grafting a vein from elsewhere in the body to completely circumvent the occluded artery in the case of bypass surgery, and may not actually improve the atherosclerosis, or reduce the amount of plaque present in the body. Thus, there exists a need for a method of reducing atherosclerotic plaque in patients who have already developed atherosclerosis.

SUMMARY

A first general aspect relates to a method for treating atherosclerosis in a patient comprising maintaining an elevated level of alcohol in the patient's blood and administering a calcium chelating agent.

A second general aspect relates to a method comprising treating atherosclerosis in a patient by administering a calcium chelating agent and an alcohol.

A third general aspect relates generally to method of treating atherosclerosis in a patient, the method comprising delivering an alcohol through an enteral feeding tube to achieve a therapeutically effective level of the alcohol in a body of the patient, maintaining the therapeutically effective level of the alcohol in the body of the patient for a predetermined treatment period, and administering a therapeutically effective amount of a calcium chelating agent to the patient at a regular interval until the predetermined treatment period ends, wherein the maintaining of the therapeutically effective level of the alcohol together with the administering of the therapeutically effective amount of the calcium chelating agent reduces an amount of plaque in a cardiovascular pathway in the body of the patient.

The foregoing and other features of construction and operation will be more readily understood and fully appreciated from the following detailed disclosure, taken in conjunction with accompanying drawings.

BRIEF DESCRIPTION OF THE DRAWINGS

Some of the embodiments will be described in detail, with reference to the following figures, wherein like designations denote like members, wherein.

DETAILED DESCRIPTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

The following disclosures pertain to embodiments of a method of treating atherosclerosis and the corresponding cardiovascular diseases by reducing atherosclerotic plaque in patients who are suffering from atherosclerosis or are at risk of cardiovascular disease. This method can be based, in part, on the discovery that consumption and/or introduction of alcohol may reduce the mortality of cardiovascular diseases caused by atherosclerosis. Accordingly, alcohol may be used for the treatment and reduction of atherosclerosis. Similarly, this method can also be based on the discovery that calcium chelating agents, such as sodium thiosulfate and analogues thereof, may increase the solubility of calcium by up to 100,000 fold and may be used to treat vascular calcification. Accordingly, a calcium chelating agent, such as sodium thiosulfate, may be used to increase the solubility of the calcium in plaque deposits for the treatment of atherosclerosis.

Figure 1:
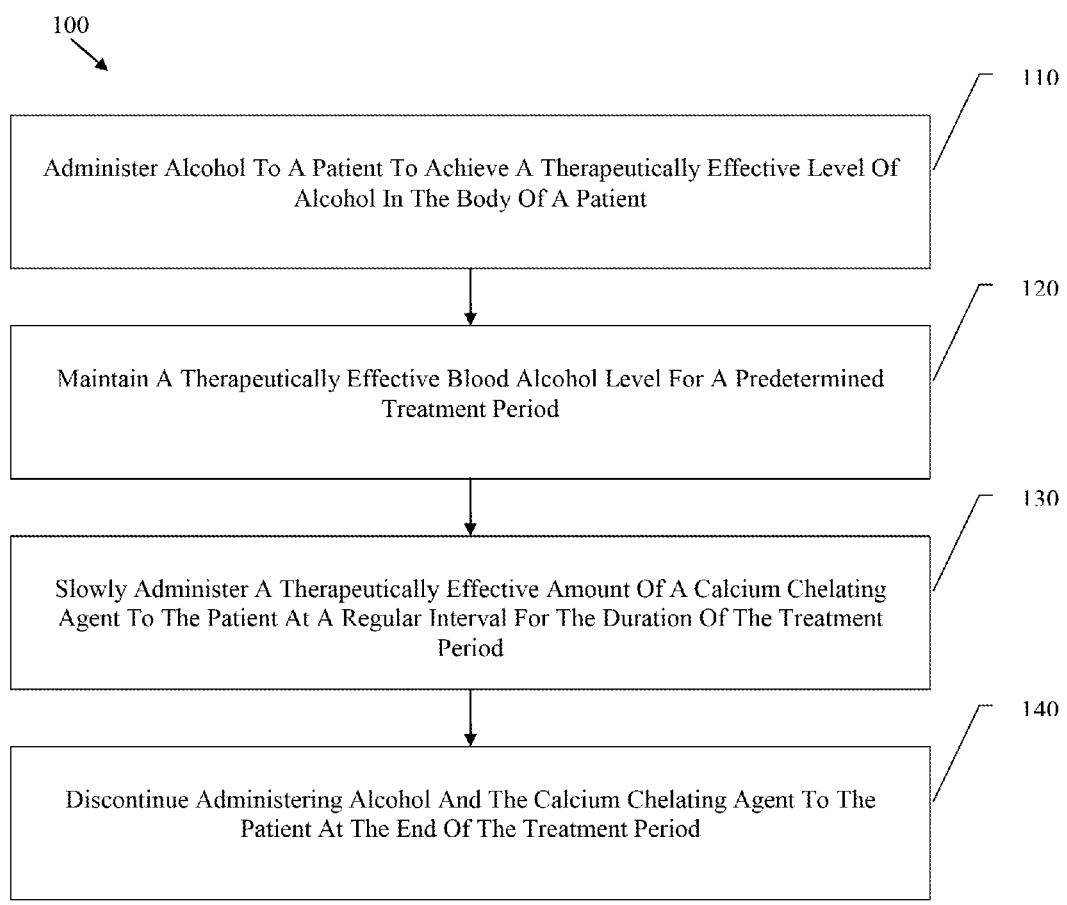
FIG. 1 depicts a process flow view of an embodiment of a method for reducing atherosclerotic plaque formations in patients suffering from atherosclerosis.

Referring to the drawings, FIG. 1 depicts an embodiment of a method for reducing atherosclerotic plaque formations in patients suffering from atherosclerosis 100. Embodiments of patients may include, but is not limited to, humans, primates, pigs, dogs, and/or any other mammal which may benefit from the methods currently disclosed. The method disclosed herein may be used for treating atherosclerosis and any corresponding cardiovascular diseases associated with atherosclerotic plaque formation. Embodiments of treatment of atherosclerosis may include modifying, dissolving, reducing, removing, and/or eliminating atherosclerotic plaque from blood vessels of cardiovascular pathways in the body, such as arteries, of patients suffering from atherosclerosis or any associated cardiovascular diseases resulting from a buildup of plaque in a cardiovascular pathway. Embodiments of the plaque targeted to be reduced, eliminated, modified, dissolved, etc., may be atherosclerotic plaque, arterial plaque, plaque, atherosclerotic lesions, a clogging agent, a hardening agent, and the like, that may cause a narrowing of a cardiovascular pathway in a mammal's system; plaque may be stable or unstable plaque.

Embodiments of method 100 may include the steps of administering alcohol to a patient to achieve a therapeutically effective level of alcohol in the blood of a patient 110, maintaining a therapeutically effective blood alcohol level for a predetermined treatment period 120, slowly delivering a therapeutically effective amount of a calcium chelating agent to the patient at regular intervals for the duration of the treatment period 130, and discontinuing administering alcohol and the calcium chelating agent to the patient at an end of the treatment period 140. Furthermore, embodiments of method 100 may include a method for treating conditions or diseases in a patient comprising maintaining an elevated level of alcohol in the patient's blood, and administering a calcium chelating agent.

Embodiments of method 100 may include administering alcohol to a patient to achieve a therapeutically effective level of alcohol in the blood of a patient 110. Embodiments of the alcohol may include organic compounds with a hydroxyl group attached to a carbon atom, such as ethanol, or any other alcohol which may produce the desired therapeutic effects in patients. In addition, the alcohol may be comprised of one or more alcohols. Embodiments of ethanol as the alcohol used in method 100 may include ethanol in liquid form, or dissolved in aqueous solution, for example, a 20% ethanol aqueous solution. However, the alcohol may be an ethanol of less than 20% ethanol aqueous solution, more than 20% ethanol aqueous solution, such as 80% ethanol aqueous solution, or even a higher % ethanol in liquid form or aqueous solution. Embodiments of administering alcohol may include administering alcohol through an enteral feeding tube. Embodiments of enteral feeding tubes may include nasoduodenal tubes, which may be a flexible tube which is passed proximally through the nose and distally into the small intestine. The level of alcohol in a patient's body may be expressed as a gram-percentage of alcohol in the blood, a blood-alcohol content, a percent of alcohol in the blood, or any other method of quantifying an amount of alcohol in a patient's system. Embodiments of determining the level of alcohol in the patient's body may include analysis of the patient's blood, breath, or any other accurate and reliable means of analyzing levels of alcohol in a patient's body.

Furthermore, embodiments of method 100 may include achieving a therapeutically effective level of alcohol in the patient's blood 110. Embodiments of a therapeutically effective level of alcohol may be a gram-percent of alcohol between 0.10 and 0.50 gram-percent of alcohol. In another embodiment, a therapeutically effective level of alcohol may be a gram-percent of alcohol no more than 0.4 gram-percent of alcohol. In yet another embodiment, the therapeutically effective level of alcohol may be a gram-percent of alcohol may be a minimum of 0.3 gram-percent of alcohol. In another embodiment, the therapeutically effective level of alcohol may be a gram-percent of alcohol may be between 0.3-0.4 gram percent alcohol. In yet another embodiment, the therapeutically effective level of alcohol may be a gram-percent of alcohol may be a minimum of 0.4. However, other levels of alcohols in the blood may be therapeutically effective depending on the size, age, health, species, etc., of the patient, as well as the length of time of exposure or presence of alcohol in the patient's system. For instance, a particular patient may be administered an amount of alcohol to maintain or achieve a gram-percent of alcohol that is outside the range 0.10 and 0.50 while still being therapeutically effective because of a characteristic of the patient and/or a treatment length. In one embodiment, a 20% ethanol aqueous solution may be administered to the patient through a nasoduodenal tube until a 0.40 gram-percent of alcohol in the blood is achieved. Those skilled in the art should appreciate that there may be other embodiments of administering alcohol to a patient, such as ingesting liquid alcohol, inhaling alcohol in gaseous form, or injecting alcohol intraperitoneally, or injecting alcohol intravenously, to achieve a therapeutically effective amount of alcohol in the blood.

With continued reference to FIG. 1, embodiments of method 100 may also include maintaining a therapeutically effective level of alcohol in the patient's blood for a predetermined treatment period 120. The therapeutically effective level of alcohol may be a constant level during the predetermined amount of time. Alternatively, the therapeutically effective level may intentionally vary during the predetermined amount of time. However, those skilled in the art should understand that embodiments of maintaining a constant therapeutically effective level of alcohol may vary slightly from the constant level during administration of the alcohol to the patient, yet still be considered a constant level. Moreover, embodiments of a predetermined treatment period may be a length of time in which the patient is treated in accordance with one or more steps of method 100. For instance, the predetermined treatment period may include a number of days, such as 10 days, 20 days, or 30 days that the method 100 is performed. There may be an initial period before the predetermined treatment period begins in which the patient's blood alcohol level is initially brought to the therapeutically effective level of ethanol, and once the initial period is over, and the patient reaches the therapeutically effective level of ethanol, the predetermined treatment period may begin. Embodiments of the initial period may be between 0-5 days, or longer depending on the patient and/or other occurrences, such as a complication, a precaution, a stoppage, and the like.

Embodiments of maintaining a constant level of alcohol in the patient's blood may further include administering alcohol to the patient at a calculated rate to keep the blood alcohol level constant. Embodiments of a calculated rate of alcohol administration may include a rate based upon the alcohol clearance rate of the patient. For instance, in an exemplary embodiment, the alcohol clearance rate may include 24.7 mg of alcohol per kilogram of the patient's body weight per hour. Maintaining a level of alcohol in the patient's blood may include maintaining the level of alcohol in the patient's blood at the desired therapeutically effective level, as described above. Embodiments of maintaining a constant level of alcohol in the patient's blood may also include maintaining the level of alcohol in the patient's blood within a specified range. An exemplary embodiment of a specified range may include 0.40±0.10 gram-percent of alcohol in the patient's blood.

Furthermore, embodiments of maintaining a constant level of alcohol in the patient's blood may include maintaining a level, constant or otherwise, of alcohol in the patient's blood for a daily portion of time during the predetermined period of time the method 100 is performed. For example, the level of ethanol in the patient's body may be maintained for a certain number of hours in a day, for a predetermined number of days. In other words, method 100 may be performed over a predetermined period of time, such as 30 days, while maintaining the alcohol at a therapeutically effective level for 12 hours a day. Other embodiments of method 100 may be performed for a predetermined period of time (e.g. 30 days) while the alcohol level is maintained at a therapeutically effective level for 24 hours a day for the duration of the treatment period, or for a substantial portion of each day for the duration of the treatment period. While embodiments of method 100 may be performed over a predetermined amount of time, such as 30 days, the method 100 may be discontinued, ended, stopped, paused, suspended, continued, performed, etc. for some time prior or after the predetermined amount of time, for various reasons, including medical reasons, effectiveness of method, and the like. Embodiments of maintaining a level of alcohol in the patient's blood may also include determining, checking, monitoring, etc., the patient's blood alcohol level a least once a day to ensure that the level of alcohol is remaining steady, or at a targeted level whether constant or variable. Embodiments of determining the level of alcohol in the patient's blood may be the same as those mentioned above. In one embodiment, the patient's blood alcohol level is analyzed once a day, and the patient is given a 24.7 mg dose of alcohol per kilogram of patient's body weight per hour, 24 hours a day, to maintain the patient's blood alcohol level of 0.40 gram-percent for 30 days. Those skilled in the art should appreciate that there may be other embodiments of maintaining a constant level of alcohol in the patient's blood.

Referring still to FIG. 1, embodiments of method 100 may include administering, slowly or otherwise, a therapeutically effective amount of a calcium chelating agent to the patient at a regular interval for the duration of the predetermined treatment period 130. A calcium chelating agent may include any agent, substance, element, composition, and the like, which can bind to calcium and increase the solubility of calcium. Embodiments of a calcium chelating agent may include sodium thiosulfate, sulfated analogues of sodium thiosulfate, such as potassium thiosulfate, lithium thiosulfate, or any other sulfated sodium salt which may increase the solubility of calcium deposits. Calcium chelating agents may also include any agent, substance, element, composition, and the like, which can undergo a sulfating reaction with calcium to create a sulfated calcium salt. Furthermore, calcium chelating agents may include any agent, substance, element, composition, and the like, which may react with calcium to form a soluble calcium salt. Embodiments of the resulting soluble calcium salts may include calcium chloride or calcium gluceptate. Embodiments of a calcium chelating agent may also include reducing agents, wherein a reducing agent may be any agent, substance, element, composition, and the like, which may donate an electron, or is oxidized, in an oxidation-reduction reaction. Reducing agents may also include any agent that causes calcium to accept an electron, or causes calcium to be reduced in an oxidation-reduction reaction. It should be noted that the methods and compounds presently contemplated are distinct from the chelating agents and chelation therapy advocated by the American College for Advancement in Medicine.

Embodiments of administering a calcium chelating agent may include administering a calcium chelating agent intravenously through a catheter. However, other medical means may be used to safely administer and/or introduce a calcium chelating agent into a body of a patient, such as ingestion, ingestion with a carrier, a stent with a time release capsule inserted during angioplasty for localized treatment, ingestion, or intraperitoneal injection. Embodiments of a therapeutically effective amount of a calcium chelating agent may be at least 25 g over a 60 minute period, between 20 g-30 g over a 60 minute period, and no more than 25 g over a 60 minute period, wherein the 60 minute time period may be at least 60 minutes, up to 60 minutes, or between 45 minutes and 90 minutes. Further embodiments of a therapeutically effective amount of a calcium chelating agent may include 25 g, or 0.36 g of sodium thiosulfate per kilogram of the patient's body weight. Other embodiments of a therapeutically effective amount of a calcium chelating agent may also include a range between 20-30 g of sodium thiosulfate, or between 0.3 g-0.4 g of sodium thiosulfate per kilogram of the patient's body weight. Moreover, the calcium chelating agent may be administered at regular intervals, wherein a regular interval may be every other day, or other length of time in between administering the calcium chelating agent. For instance, embodiments of a regular interval may include every other day, every third day, or once a week. Embodiments of slowly administering a calcium chelating agent may also include administering the desired amount of the calcium chelating agent over an administering period, wherein the administering period may be a 60 minute period. However, those having ordinary skill in the art should appreciate that the administering period of the calcium chelating agent may be more than 60 minutes or less than 60 minutes depending on the dosage of the calcium chelating agent, or other characteristics associated with method 100. Furthermore, embodiments of slowly administering a therapeutically effective amount of a calcium chelating agent to the patient at a regular interval for the duration of the treatment period may include administering a first dose to the patient after a desired, or therapeutically effective, level of alcohol in the patient's blood is achieved and remains constant for one day. In one embodiment, a patient may be given a 25 g dose of sodium thiosulfate, or other calcium chelating agent, intravenously every other day for 30 days, starting once the patient's blood alcohol level is stabilized at 0.40 gram-percent. Those skilled in the art should appreciate that there may be other embodiments of administering a calcium chelating agent to a patient, such as ingesting the calcium chelating agent, or injecting the calcium chelating agent subcutaneously.

Embodiments of method 100 may further include discontinuing administering alcohol and the calcium chelating agent to the patient at an end of the predetermined treatment period 140. Embodiments of discontinuing administering alcohol may include slowly lowering a maintenance dose of alcohol over a period of time until no alcohol is administered. Embodiments of slowly lowering the maintenance dose of alcohol over a period of time may include incrementally reducing the administration of alcohol over a period of time, and then completely discontinuing the administration of alcohol to the patient. Embodiments of a period of time may include 48 hours, 96 hours, or any period of time necessary to safely discontinue alcohol administration. Embodiments of discontinuing administering a calcium chelating agent may include discontinuing administering the calcium chelating agent to the patient at the end of the treatment period. In one embodiment, at the end of a 30 day predetermined treatment period, the patient is no longer administered any sodium thiosulfate, and the maintenance dose of 49.4 mg alcohol per kilogram of patient's body weight per hour may be reduced to 24.7 mg of alcohol per kilogram of patient's body weight for 24 hours, and then may be reduced to 12.4 mg of alcohol per kilogram of patient's body weight for 24 hours, at which time alcohol administration is discontinued completely. Those skilled in the art should appreciate that there may be other embodiments of discontinuing administering alcohol and a calcium chelating agent to the patient, such as discontinuing the administration of the calcium chelating agent and alcohol, and administering 5 mg of diazepam intravenously to the patient every 6 hours for 48 hours. For example, the maintenance dose of alcohol per kilogram of patient's body weight per hour may be between 45-55 mg and may be reduced to 23-29 mg of alcohol per kilogram of patient's body weight for 24 hours, and then may be reduced to 12.4 mg of alcohol per kilogram of patient's body weight for 24 hours. Various dosages may be used during discontinuing period to effectively treat the patient.

Moreover, supportive care, including one or more prescription drugs, may be administered to the patient during the treatment period. For instance, one or more prescription drugs may be given to the patient to treat cases of nausea, vomiting, vertigo, discomfort, and the like. Embodiments of method 100 may be performed in an intensive care unit or similar setting that is capable of handling various medical emergencies or standard monitoring procedures. In addition, embodiments of method 100 may include the step of providing a tracheostomy to provide ventilator or respiratory support. Embodiments of method 100 may also provide a dialysis analysis/monitoring during the calcium chelating agent administration to deal with calcium and other electrolyte issues. At the end of the predetermined treatment period, follow-up radiologic studies (e.g., angiography, CT-scan, an MRI-scan procedure) may be performed to determine the amount of reduction of atherosclerosis. If the reduction of atherosclerosis plaque is insufficient, or a physician determines that the remaining amount is unhealthy for the patient, method 100 may include the step of re-administering the steps described above with respect to method 100.

Over the course of the treatment period of method 100, the alcohol and calcium chelating agent may dissolve, or otherwise eliminate, the atherosclerotic plaque in the blood vessels of a cardiovascular pathway of a patient. The dissolved plaque may then be eliminated from the patient's body through various metabolic processes and organs such as the liver and kidneys. The elimination of the atherosclerotic plaque from the interior walls of blood vessels may widen the interior of the blood vessels, increase blood flow through those vessels, reduce atherosclerosis, and decrease the risk of cardiovascular diseases associated with atherosclerosis.

Example 1 is an exemplary embodiment of the steps of method 100:

EXAMPLE 1

A 110 kg human male patient is sedated, and a nasoduodenal tube is introduced into the patient's nostril and guided into position. About 1 L of 40% ethanol aqueous solution is administered to the patient to achieve a blood ethanol level of 0.40 gram-percent during an initial period. The patient's blood is analyzed to ensure that the desired blood ethanol level has been achieved, and then the predetermined treatment period of 30 days is started. Thereafter, about 16 ml of 20% ethanol aqueous solution is administered every hour to maintain the steady-state blood ethanol level of 0.40 gram-percent. The patient's blood is analyzed once a day every day thereafter to confirm the blood ethanol level is remaining constant. After the first day of achieving a steady-state blood ethanol level of 0.40 gram-percent, about 25 g of sodium thiosulfate is administered intravenously to the patient over the course of one hour. This 25 g dose of sodium thiosulfate is administered every other day thereafter. This course of treatment continues for 30 days, at which time the maintenance dose of ethanol and the intravenous sodium thiosulfate are discontinued, and the patient receives a 5 mg dose of diazepam every 6 hours for 48 hours. The patient is then subjected to follow-up radiological studies to determine the amount of atherosclerotic plaque reduction.

Figure 2:
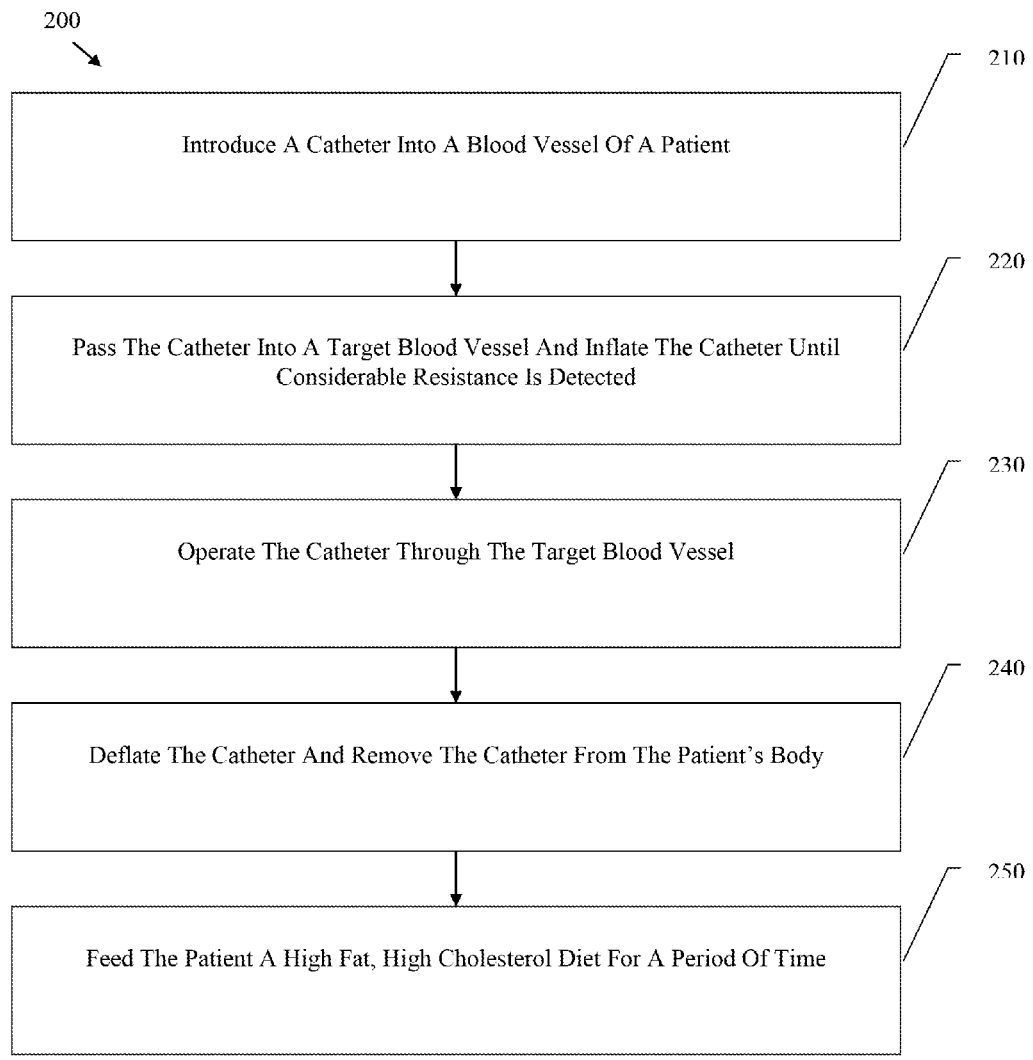
FIG. 2 depicts a process flow view of an embodiment of a method for inducing atherosclerosis in patients.

Referring still to the drawings, FIG. 2 depicts an embodiment of a method for inducing atherosclerosis in a patient 200. The method 200 disclosed herein may be used for inducing atherosclerosis in a patient for the purposes of testing method 100. In most embodiments, the patient is a pig or other non-human mammal; however, it is contemplated that the patient could be human, and the steps of method 200 could be performed on a human. Embodiments of method 200 may include the steps of introducing a catheter into a blood vessel of a patient 210, passing the catheter into a target blood vessel and inflating the catheter until a considerable resistance to movement is detected 220, operating the catheter through the target blood vessel 230, deflating the catheter and removing the catheter from the patient's body 240, and feeding the patient a high fat, high cholesterol diet for a period of time 250. Furthermore, embodiments of method 200 may include a method for inducing atherosclerosis in a patient comprising disrupting an endothelial layer of a blood vessel of the patient, and feeding the patient a high fat, high cholesterol diet for a period of time.

Embodiments of method 200 may include the step of introducing a catheter into a blood vessel of a patient 210. Embodiments of a catheter may be a balloon catheter, a soft catheter, an inflatable catheter, and the like. Specific embodiments of the catheter may be a 5 F Fogarty arterial embolectomy catheter. Embodiments of a blood vessel of a patient may include one of the patient's femoral arteries, one of the patient's carotid arteries, or a cardiovascular pathway of the body. Moreover, embodiments of introducing a catheter into a blood vessel of a patient may include exposing the blood vessel of the patient, making a small incision in the blood vessel of the patient and inserting the catheter, in accordance with modern, conventional medical procedures. In one embodiment of method 200, an incision is made to expose a pig's right carotid artery, and then a small incision is made in the carotid artery and a 5 F Fogarty arterial embolectomy catheter is inserted into the carotid artery. Those skilled in the art should appreciate that there may be other embodiments of introducing a catheter into a blood vessel of a patient.

Embodiments of method 200 may also include passing the catheter into a target blood vessel and inflating an inflatable or balloon-like portion of the catheter until a considerable resistance to movement is detected 220. An embodiment of a target blood vessel may include the abdominal aorta. Embodiments of inflating the balloon-like portion of the catheter may be accomplished with saline. Embodiments of inflating the balloon until considerable resistance is detected may include filling the catheter, in particular, the inflatable or balloon-like portion of the catheter, with 2 ml of saline and then pulling firmly on the catheter to test the resistance. Those skilled in the art should appreciate that there may be other embodiments of passing a catheter into a target blood vessel and inflating the balloon.

Furthermore, embodiments of method 200 may include operating the inflated catheter through the target blood vessel 230. Operating the inflated catheter may include moving the catheter back and forth several times through the target blood vessel, and may also include actuating, moving, directing, facilitating, and the like, of the catheter within the patient. Embodiments of operating the inflated catheter back and forth may include passing an inflated balloon catheter along an entire length of the target blood vessel or only a small portion of the target blood vessel. Embodiments of operating or moving the inflated balloon catheter back and forth several times through the target blood vessel may include moving the inflated balloon catheter back and forth as many times as thought necessary to realize the amount of desired distension of the target blood vessel; the desired amount of distension may include the amount of distension required to induce atherosclerosis in the patient.

With continued reference to FIG. 2, embodiments of method 200 may also include deflating the inflatable portion of the catheter and removing the catheter from the patient's body 240. Embodiments of deflating the balloon may include draining the 2 ml of saline used to inflate the balloon. Embodiments of removing the catheter may include removing the balloon catheter from the same incision used to insert the balloon catheter. In one exemplary example, the saline is drained from the catheter, and then the catheter is removed from the patient's body via the same incision used to insert it, and then the incisions are closed. Embodiments of closing the incisions may include sutures, staples, tapes, adhesives, or any other embodiment of a method which comports with modern, conventional medical procedures used to close surgical incisions. Those skilled in the arts should appreciate that there may be other embodiments of deflating and removing the balloon catheter from the patient's body.

Still further, embodiments of method 200 may include feeding the patient a high fat, high cholesterol diet for a period of time 250. Embodiments of feeding may include ingestion, enteral feeding, parenteral feeding, or any other method which causes the desired diet to be received by the patient. One specific embodiment of a high fat, high cholesterol diet may be 17 g of peanut oil, 10 g of elaidic acid, 5 g of corn oil, 400 g of whole milk powder, 41 g of casein, 153 g of corn starch, 10 g of cholesterol, 8 g of sodium cholate, 10 g of salt mix, 10 g of vitamin mix, and 64 g of alphacel. However, a range of foodstuffs may be consumed by the patient to induce atherosclerosis. The high fat, high cholesterol diet may be administered for a length of time necessary to exhibit at least signs of atherosclerosis in the patients cardiovascular pathway(s). For instance, the patient may be administered a high fat/high cholesterol diet for a period of time including one or month, 3 months, 6 months, 1 year, or any period of time necessary to induce atherosclerosis in the patient. Those skilled in the arts may appreciate that there may be other embodiments of feeding a patient a high fat, high cholesterol diet for a period of time. Over the course of the period of time the patient is fed the high fat, high cholesterol diet, the disruption of the endothelial layer of the blood vessel caused by distending the blood vessel with the catheter combined with the ingestion of the high fat, high cholesterol diet may cause atherosclerotic plaque to form in the patient's blood vessel. The accumulation of the atherosclerotic plaque on the interior walls of the blood vessel may narrow the interior of the blood vessel, decrease blood flow through the vessel, and induce atherosclerosis in the patient. The creation of atherosclerosis in the patient will allow for method 100 to be tested.

Example 2 is an exemplary embodiment of the steps of method 200:

EXAMPLE 2

An 8 week old Yorkshire Swine weighing 11 kg is anesthetized with halothane. An incision is made to expose the pig's right carotid artery. A nick is made in the artery, and a 5 F Fogarty arterial embolectomy catheter is inserted. The catheter is passed into the pig's abdominal aorta and then inflated with about 2 ml of saline until considerable resistance to movement is detected. The inflated balloon is passed back and forth several times through a portion of the length of the pig's abdominal aorta to distend the aorta and disrupt the endothelial layer. The balloon is deflated and removed from the pig. For 6 months thereafter, the pig is fed a high fat, high cholesterol diet consisting of 17 g of peanut oil, 10 g of elaidic acid, 5 g of corn oil, 400 g of whole milk powder, 41 g of casein, 153 g of corn starch, 10 g of cholesterol, 8 g of sodium cholate, 10 g of salt mix, 10 g of vitamin mix, and 64 g of alphacel.

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the invention, as required by the following claims. The claims provide the scope of the coverage of the invention and should not be limited to the specific examples provided herein.

The claims are as follows:

1. A method for treating atherosclerosis in a patient comprising: administering an alcohol to the patient, maintaining a minimum blood alcohol level of 0.3 grams alcohol per 100 milliliters of blood in the patient for a treatment period of at least ten days; and administering a calcium chelating agent to the patient during the treatment period.

2. The method of claim 1, wherein the calcium chelating agent is sodium thiosulfate or any analogue thereof.

3. The method of claim 1, wherein the alcohol is administered to the patient through a nasoduodenal tube.

4. The method of claim 1, wherein the alcohol is ethanol.

5. The method of claim 1, wherein the blood alcohol level of the patient is maintained for at least a portion of a day.

6. The method of claim 5, wherein the portion of the day comprises the entire day.

7. The method of claim 1, wherein administering the calcium chelating agent comprises administering the calcium chelating agent at a regular interval.

8. The method of claim 7, wherein the regular interval comprises every other day.

9. The method of claim 1, wherein the number of days of the treatment period is more than thirty.

10. A method of treating atherosclerosis in a patient, said method comprising administering a calcium chelating agent at a regular interval at least every other day while administering an alcohol to the patient so that to maintain a minimum blood alcohol level of 0.3 grams alcohol per 100 milliliters of blood.

11. The method of claim 10, wherein the calcium chelating agent is sodium thiosulfate or any analogue thereof.

12. The method of claim 10, wherein the calcium chelating agent is a reducing agent.

13. The method of claim 10, wherein the alcohol is administered through a nasoduodenal tube.

14. The method of claim 10, wherein the blood alcohol level is maintained for a portion of a day during a treatment period.

15. The method of claim 10, wherein the alcohol is ethanol.

16. A method of treating atherosclerosis in a patient, the method comprising:
  delivering an alcohol to the patient through an enteral feeding tube to achieve a blood alcohol level of a minimum of 0.3 grams ethanol per 100 milliliters of blood;
  maintaining the blood alcohol level for a predetermined treatment period of at least three days; and
  administering at least 25 grams of a calcium chelating agent to the patient at a regular interval until the predetermined treatment period ends;
  wherein maintaining the blood alcohol level and administering the therapeutically effective amount of the calcium chelating agent reduces an amount of plaque in a cardiovascular pathway in a body of the patient.

17. The method of claim 16, wherein the regular interval is every other day.

18. The method of claim 16, wherein the steps of the method of treating atherosclerosis are repeated.

* * * * *